United States Patent [19]

Bunting et al.

[11] 4,427,631
[45] Jan. 24, 1984

[54] POVIDONE IRRADIATION

[75] Inventors: Thomas G. Bunting, Randolph; Dominic A. Centrone, Flemington, both of N.J.; Richard S. Sackler, Greenwich, Conn.; Alfred Halpern, Great Neck, N.Y.

[73] Assignee: Euroceltique, S.A., Luxembourg, Luxembourg

[21] Appl. No.: 382,380

[22] Filed: May 27, 1982

[51] Int. Cl.$^3$ .......................... C08F 8/00; B01J 19/08; A61L 2/08
[52] U.S. Cl. .................................... 422/22; 204/159.18
[58] Field of Search ............... 422/22, 23; 204/159.18, 204/159.20

[56] References Cited

U.S. PATENT DOCUMENTS

| | | | |
|---|---|---|---|
| 3,537,967 | 11/1970 | Kelley et al. | 422/22 X |
| 3,758,273 | 9/1973 | Johnston et al. | 422/23 |
| 3,940,325 | 2/1976 | Hirao | 422/22 |
| 4,110,185 | 8/1978 | Williams et al. | 204/159.20 |
| 4,274,932 | 6/1981 | Williams et al. | 204/159.20 |

FOREIGN PATENT DOCUMENTS 7736 2/1980 European Pat. Off. ....... 204/159.18

OTHER PUBLICATIONS

Charleshy, A. et al.; "Radiation Protection in Aqueous Polymer Solutions"; *Int. J. Rad. Biol.;* vol. 5; No. 6; 7-62; pp. 521-534.
Effect of Gamma-Irradiation or Disinfectant, K. Hosobuchi, et al., J. Antibact. Antifung. Agents 9(1):3-8(1981)-with translation.

*Primary Examiner*—Barry S. Richman
*Attorney, Agent, or Firm*—Steinberg & Raskin

[57] ABSTRACT

Sterilized povidone-iodine (polyvinylpyrrolidone-iodine) is obtained by irradiating povidone-iodine in the presence of iodide ions. Preferably the irradiation is effected in the presence of iodine and both iodide and iodate ions. The iodide ions, with or without iodate ions, have the effect of preventing the degradation of povidone-iodine and the gelation of iodine and povidone.

13 Claims, No Drawings

POVIDONE IRRADIATION

BACKGROUND OF THE INVENTION

Polyvinylpyrrolidone is the homo-polymer of 1-ethylenyl-2-pyrrolidinone also known as 1 vinyl-2-pyrrolidinone polymer of the following formula:

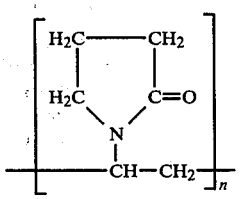

a common name for this chemical substance is povidone and the compound is sometimes designated as PVP.

Povidone is a synthetic polymer consisting essentially of linear 1-vinyl-2-pyrrolidinone groups which have been polymerized into polymer chains of various molecular weights, generally having mean molecular weights ranging from about 10,00 to 700,000 although polymers of both lesser and higher molecular weights are known.

Providone is available as an article of commerce, either as a dry powder or in aqueous solution for use in a wide variety of chemical, pharmaceutical and food manufacturing processes as well as special industrial compositions such as inks, paints and emulsions, cosmetics and germicidal products. Povidone is used for example in the manufacture of adhesives to improve strength and toughness; in cosmetic products to condition and protect skin and hair; in pharmaceutical manufacture as a tablet binder, coating agent, dispersant and protective colloid; in the manufacture of plastics as a pigment dispersant, bonding agent, and stabilizer; in paper manufacture to increase strength as well as a coating polymer and in synthetic fibers to improve dye receptivity. It is also widely employed in inks, lithography, detergents and soaps, textiles, agricultural products and as a clarifying aid.

Underriding the overall use of povidone in manufacture and formulation of different compositions is its contribution to the viscosity of the fluid medium being used. The viscosity contribution of povidone ranges from high viscosity to low viscosity and is a function of the average molecular weight of the polymer. Povidone is classified by K-values which are assigned to the various povidone polymers. These constants, i.e., K-values, are derived from viscosity measurements in accord with the well known Fikentscher's formula and the smaller the K-value, the lower the intrinsic viscosity of the polymer.

The more common commercially available povidone polymers have K-values of K-14, K-30, K-60 and K-90, and in aqueous solutions, povidone K-15 and povidone K-30 have little effect on viscosity in concentrations below 10%, whereas povidone K-60 and povidone K-90 have considerable influence on the flow properties of a solution at such concentrations. While the viscosity effect of povidone is virtually unchanged by pH, concentrated hydrochloric acid and strong alkali have been shown to influence the viscosity of povidone. Moreover, certain organic solvents have a particular effect on the viscosity contribution of povidone, the intensity of which is related to the polarity of the particular organic solvent.

Povidone forms molecular adducts or complexes with many substances to result in a solubilizing action for certain materials but also a precipitation effect for others. The povidone polymer reacts with poly-acids to form complexes that are generally insoluble in water but these may be solubilized by special treatment of the formed insoluble polymer. Cross-linkage of the povidone polymer is influenced by many diverse factors as for example, actinic light, diazo compounds, oxidizing agents and heat. Cross-linking of the povidone polymer is a serious limitation to its use since the povidone polymer is now altered into an aqueous insoluble form.

It is well known that povidone and its solutions are capable of supporting microbial growth as for example, bacteria, viruses, molds and yeast. While the usual preservatives such as benzoic acid, sorbic acid and the esters of parahydroxybenzoic acid may be used as germicides for povidone preparations, these present special limitations because of their less than broad antimicrobial spectrum and their known allergenicity. While aqueous solutions of povidone are known to be relatively stable to heat, and short interval autoclaving has been used to sterilize povidone preparations, this use of heat is also known to cause degradation of the polymer. Thus for example, povidone which is stable to moderate heat will darken in color and decreases in water solubility when heated to about 150° C. The presence of certain substances in the povidone solution will accelerate cross-linking at even lower temperatures. When a povidone solution is heated to 100° C., in the alkaline pH range, the polymer becomes permanently altered to be irreversibly insoluble. Similar cross-linked changes occur when alkaline sodium phosphate buffers are used and when an oxidizing agent such as ammonium persulfate is added to a povidone solution, cross-linking gel formation occurs in about 30 minutes when the combination is heated at moderate temperatures of about 90° C.

The cross-linking of the polymer caused by heat, oxidizing agents, salts and other substances presents special problems in the manufacture and processing of certain compositions containing povidone, when these povidone solutions are intended for parenteral use, since the formed insoluble cross-linked povidone may initiate thrombotic episodes and other noxious events. When povidone is used in the manufacture of those preparations requiring sterilization but containing oxidizing agents or other oxygen sources, then similar incompatibility occurs to limit the use of povidone in the preparations.

Gamma radiation is known to be an effective sterilizing process but is notoriously unsuited for use with povidone polymers. The literature is replete with references to the particular degradative effects of cross-linkage occurring when povidone is exposed to even minimal gamma radiation dosage. The various aspects of radiation induced changes in aqueous polymer solution have been ascribed to free radical formation and subsequently initiated chemical changes. The actions of radiation on povidone, together with radiolysis products formed in the composition, results in macroradical polymer chain formation and these macroradicals further inter-react so that the ultimate effect of radiation is either cross-linkage gelation or chain scission.

Gamma irradiation interacts with target atoms to cause one or more of three different actions, namely photo-electric effects, Compton scattering, and pair-production. As the energy dose of the gamma irradiation increases, the particular predominant effect succeeds to the next dose related responsive stage, from the photo-electric stage to the Compton scattering stage and finally to the pair-production stage. Both the photo-electric and Compton scattering effects produce highly ionizing electrons which are uniformly distributed throughout the radiation target and these influence the formation of free radicals and ionic reactions. It is the combination of these reactions in the vicinity of contaminent microorganisms that brings about the lethal efficacy or sterilizing properties of irradiation processes.

When povidone solutions are irradiated with gamma radiation, gelation occurs when the concentration of povidone in solution is above the critical limit of from 0.3% to 1% by weight of povidone, dependent upon the molecular weight. For the lower molecular weights of K-30 and below the critical concentration factor is between 0.5% and 1% by weight while for values above K-30 this critical concentration is between 0.3% and 0.5%. Below this critical concentration limit, macrogelation to form a wall-to-wall gel, is not readily observed. For intermolecular cross-link formation, the polymer chains must be in close proximity to each other. In dilute solutions, the mobility of polymer chains is increased and while some chains are deactivated by the radiolysis products of water before they achieve intermolecular linkage, the increased mobility of the polymer chain will increase the probability of intermolecular cross-linking when irradiated. Furthermore, in dilute solutions the smaller polymer chains react with the radiolytic by-product of water to reduce gel formation. Thus gelling does not occur below the critical concentration limits.

In dilute poly-electrolyte solutions, the polymer products become ionized to increase the overall gelation effect of the polymer. Oxidative degradation is associated with a decrease in viscosity that is generally observed in the early stages of the irradiation of povidone, and a subsequent increase in viscosity occurs as intermolecular cross-linking overtakes the first phases of intramolecular linking and chain scission. As the intermolecular cross-linking progresses under further radiation dosage, the overall effect is a decrease in viscosity through microgel unit formation and the solution becomes turbid.

The sensitivity of povidone to low doses of gamma radiation is so pronounced that adverse gelation cross-linkage effects are observed after irradiation with doses as low as 0.1 kilrad, when the particular critical concentration of povidone in solution is exceeded. The use of povidone in most industrial, agricultural and pharmaceutical manufacturing procedures exceeds the critical concentration limits established for povidone. The critical concentration level for povidone is further adversely modified by ionizing solutions, oxidizing agents and pH. This destructive, degradative response of povidone to gamma radiation which destroys its desirable properties in the formulation eliminates the use of gamma radiation as a means to render povidone and povidone-containing compositions free of microbial contamination.

Thus, attempts to produce sterilized povidone-iodine by irradiation of the povidone prior to formation of the povidone-iodine has been unsuccessful because of the above described undesirable action of the irradiation on the povidone.

On the other hand, the sterilization of povidone-iodine after formation thereof is found to be unsatisfactory because the irradiation has the effect of decreasing the amount of available iodine with consequent reduction in antibacterial activity.

SUMMARY OF THE INVENTION

It is accordingly a primary object of the present invention to provide for the production of sterilized povidone-iodine without gelation of solutions thereof and without loss of available iodine with consequent reduction in antibacterial activity.

It is yet a further object of the present invention to provide for gamma radiation by cobalt-60 gamma radiation, of povidone-iodine in the presence of iodides, the irradiation effecting sterilization without gelation of the povidone and without degradation of the povidone-iodine.

It is yet another object of the present invention to provide for the direct sterilization of solutions of povidone-iodine by gamma radiation of such solution in the presence of iodide ions.

Other objects and advantages of the present invention will be apparent from a further reading of the specification and of the appended claims.

With the above and other objects in view, the present invention mainly comprises the subjecting of povidone-iodine to gamma radiation in the presence of iodide ions in an amount sufficient to prevent degradation of the povidone-iodine.

In accordance with the preferred embodiment of the present invention, iodate ions are present along with the iodide ions, it having been found that that the iodate ions potentiate the action of the iodide ions to prevent degradation of the povidone-iodine upon gamma radiation so that a substantially lesser amount of iodide ions can be used under these circumstances.

It was unexpectedly found that povidone and povidone-containing compositions are protected against the degradative cross-linkage gelation induced by gamma radiation by the presence of iodine and of iodide ions. The ratio of iodine:iodide may vary from 100:1 to 1:100 depending upon the amount of povidone polymer being irradiated and the ionizing solvent used.

This protective effect is co-dependent on the relationship between the elemental iodine and iodide-ion and is influenced by the presence of substances capable of forming free radicals and radiolysis by-products as well as the intensity of the gamma radiation dosage used. Thus, with the use of povidone powder, although containing minimal amounts of moisture necessary to form free radicals, and radiolysis by-products, protection against cross-linage of the polymer is achieved with very low ratios of iodine even with gamma radiation intensity as high as 30 megarads.

However, when a polar solvent, as for example, water, alcohol, acetone, glycols and/or mixtures of these, is used to prepare a solution of povidone intended to be irradiated, then larger amounts of iodine and iodide ion are necessary to obtain the desired protective action against cross-linkage gelation due to gamma radiation. Thus a 15% by weight, aqueous solution of povidone K-30 will require an amount of iodine of from 0.1% to 20% by weight of iodine based on the povidone content and from 0.01 part to 100 parts by weight of iodine ion, per part of iodide, to achieve the desired protective action.

It was further found that the lower molecular weight range of povidone, as for example, the polymers below that of K-20, required lesser amounts of iodine-iodide ion to achieve the same degree of protective action than were required for higher molecular weight preparations containing povidone polymers above K-30. Thus about 0.1% by weight of iodine, based on the amount of povidone K-10 or smaller molecular weight polymer dissolved in aqueous or alcoholic soultion, in the presence of 0.01 part by weight of iodide ion will protect against cross-linkage gelation induced by gamma radiation when the dosage level was from 2 to 5 megarads. However, at least 1.0% by weight of iodine, based on the amount of povidone polymer in aqueous or alcoholic solution and from 0.1 part to 10 parts by weight of iodide ion, based on the iodine content present, will be required to achieve the same level of protective action, at an irradiation dose level of 2 megarads or higher when the molecular weight of the povidone polymer is K-30 or higher.

The optimal effective ratio of iodine to iodide ion used to protect against the noxious effects of gamma radiation when doses of up to 30 megarads are used, is from one-tenth part by weight iodide ion to 10 parts by weight of iodide ion for each part by weight of iodine used, with a preferred ratio of 1:2. When the proportion of iodine to iodide ion ratio to the povidone is less than the ratios described above, then cross-linked polymer chain gelation results together with radiolysis. When the iodine to iodide ion ratio relative to the povidone concentration exceeds the ratio set forth above, then the photo-electric and Compton scattering effects and induced free radical reactivity renders the composition being treated unsuitable for its intended use because of chain scission.

The pH of the povidone preparation does not influence the protective effect exerted by the elemental iodine-iodide system described unless such pH acts to destroy the iodine content and thereby modifies the ratio of iodine to iodide ion. Moreover, the presence of oxygen which is well known to catalyze cross-linkage of polymer solutions, does not negate the protective effects of the elemental iodine-iodide ion system and under certain circumstances, will even enhance it.

It was found that the presence of iodate ion, a strong oxidizing agent, acts to synergize the protective effects of the iodine-iodide ion system so that for each part of iodate-ion present in the solution, a lesser amount of iodide ion in proportion to the iodine content is required. This effect of the iodate ion to synergize the protective effects of iodine-iodide ion is so pronounced that the amount of iodide ion in proportion to iodine content may be lowered two-fold for each part of iodate ion present to result in an effective ratio of one part iodine for each part iodate ion and at least 0.25 parts of iodide ion.

In practice the iodine used in combination with the iodide ion to achieve the protective effects against the cross-linked polymer gelation resulting from irradiation of povidone may be either amorphous or crystalline elemental iodine, and in the solid state or in solution. The quantity of iodine used to achieve the protective effect is based upon the weight of the povidone polymer present, influenced by the radiation dosage selected. Generally, the molecular weight of povidone K-30 will be found to be a dividing point so that polymers of greater molecular weight than K-30 will require greater amounts of iodine to iodide ion than will those polymer solutions prepared with a molecular weight below K-30 when the radiation dose is kept constant.

In view of the limited aqueous solubility of elemental iodine, the complexed water soluble forms of elemental iodine may be utilized in place of the elemental iodine. The amount of such complexed water soluble forms of iodine to be used in place of the elemental iodine is based on its available iodine content which is determined by titration with standard thiosulfate or arsenite test solution. The amount of available iodine thus determined is used as an equivalent weight to the amount of elemental iodine. Such complexed water soluble forms of elemental iodine as iodophors, Lugol's solutions and other aqueous iodine solutions may be used in place of elemental iodine.

The source of iodide ions may be either inorganic or organic iodide salts capable of releasing iodide ions in a polar solvent and mixtures of these. A preferred source of the iodide ions is the inorganic iodide salts, such as sodium iodide, potassium iodide and other similar soluble iodide salts. The iodate ion may also be used to provide an activating effect to the iodine in the same manner and along with the iodide ion and it may be used in the same quantities by weight as the inorganic iodide salts. It will be found that a synergistic effect occurs in the presence of iodate ion so that an improved effect results even with minute quantities of iodide ion provided that iodate ions are also present. As a rule, the iodide ion content may be reduced two-fold for each part of the iodate ion present.

In practice the material to be irradiated is exposed to a gamma radiation source through any one of a variety of transport processes. However, neither the gamma radiation source nor the particular exposure transport process used are critical to the protective action of the iodine-iodide ion system against cross-linkage polymer gel formation of povidone. Protection against the loss of variable iodine is effected by the presence of the iodide ion along with the iodine or the presence of both iodide and iodate ions along with the iodine.

The gamma radiation dose to be utilized is based upon the expected level of microbial contamination and a reduction in the microbial count of greater than $10^6$ will be achieved with radiation dosages of from 0.1 megarad to 5 megarads. Preferably, a target gamma radiation dose of less than 2 megarads is used. This radiation dosage may be contributed by any appropriate gamma irradiation source but because of convenience, availability and cost, the cobalt 60 gamma radiation is a preferred source for irradiation.

When either povidone powder or an aqueous solution of povidone is intended to be irradiated, then the appropriate quantity of elemental iodine and iodide ion are added directly to the composition being irradiated. The iodine-iodide ion additive material are blended with the povidone composition so that a uniform dispersion results. When the powder form of povidone is to be irradiated, then the appropriate quantity of the iodine-iodide ion is added to the powder and the whole intimately mixed to achieve a uniform dispersion.

When an aqueous or polar solvent solution of povidone is intended to be irradiated then the iodine-iodide ions are dissolved directly in the povidone solution and the whole stirred until dissolved. It is found preferable to first dissolve the iodide ion in the aqueous povidone solution before adding the elemental iodine, but when an alcoholic solution is used, then the reverse order of mixing is found useful in that the iodine is to be dissolved before the iodide ion is added.

After irradiation of povidone, and solutions and formulations containing povidone, these are found to be free of microbial contamination. The povidone polymer is essentially unchanged in molecular weight and other important physical and chemical properties. A comparison by means of gel permeation chromatography and viscosity measurements of the molecular weight of an aqueous povidone composition before and after irradiation in the presence of a preferred quantity of iodine-iodide ion reveals the absence of cross-linked polymers and an essentially unchanged povidone when compared to the non-irradiated polymers. When the non-irradiated polymer, povidone solution, is irradiated without the iodine-iodide ion protective adduct, marked gelation occurs to render the non-protected povidone solution useless. Thus, it is established that the irradiation of a povidone solution in the presence of a preferred ratio of iodine and iodide ion at gamma radiation dosage levels of up to 30 megarads does not result in cross-linked polymer gel formation and there is no change in the molecular weight and no change in the viscosity measurements essential to the particular preparation being irradiated. Furthermore, the povidone solution is rendered free of microbial contamination even when challenged by the addition prior to irradiation of greater than $10^6$ microbes.

DESCRIPTION OF PREFERRED EMBODIMENTS

The following examples are given to illustrate the present invention. The scope of the invention is not, however, meant to be limited to the specific details of the examples.

EXAMPLE 1

To 100 ml of a 10% by weight aqueous solution of povidone K-30 innoculated to contain $10^6$ to $10^7$ of B. pumilus spores per ml., was added 0.1 gms. of sodium iodide. It was stirred until dissolved and then, with stirring, 0.5 gms. of elemental iodine were added. The mixture was irradiated with Cobalt 60 gamma radiation at a dosage level of 30 megarads. The resultant solution may be used in further manufacture or packaged for use for application to skin of animals and humans.

On testing the above described irradiation solution of povidone (test product A) was found to be sterile and without modification in physical properties. When it was compared to a 10% by weight aqueous solution of povidone K-30 prepared in the same manner but which was not irradiated (test product B), the following properties were observed:

| Property | Test Product A Irradiated | Test Product B Non-Irradiated |
|---|---|---|
| Viscosity | 1.05 at 25° C. | 1.05 at 25° C. |
| Cross-linked Polymers | Absent | Absent |
| No. Molecular Wt. Avg. | 29,000 | 29,000 |
| Surface Tension | 70 dynes/cm$^2$ | 70 dynes/cm$^2$ |
| Appearance | Clear | Clear |

A 10% by weight aqueous solution of povidone was then prepared with the same raw material but without the addition of iodine-iodide ion protective material (test product C) and irradiated with a dose of 30 megarads Cobalt-60 gamma radiation. When this solution was compared to the irradiated povidone-iodine-iodide solution (test product A) described above, the following results were observed:

| Property | Test Product A (Irradiated) | Test Product C (Irradiated) |
|---|---|---|
| Microbial Contamination | Sterile | Sterile |
| Viscosity | 1.05 at 25° C. | Gel |
| Cross-linked Polymers | None | Present (gel) |
| No. Molecular Wt. Avg. | 29,000 | Gel-In excess of 1 million |
| Surface Tension | 70 dynes/cm$^2$ | Not measurable |
| Appearance | Clear | Solid gel |

EXAMPLE 2

To a 5% by weight solution of povidone K-60 was added 0.25% by weight of povidone-iodine and 0.025% by weight of lithium iodide. The solution was irradiated with gamma radiation at a dosage level of 5 megarads. The resultant irradiated solution had the following properties:

| | |
|---|---|
| Viscosity at 25° C. | 1.130 |
| Surface Tension | 70 dynes/cm$^2$ |
| Cross-linked Polymers | Absent |
| No. Average Molecular Weight | 58,000 |
| Appearance | Clear Solution |

These values were essentially the same as for the non-irradiated, retained sample of the same solution which served as a control. A second control solution prepared without iodide ion, gelled when irradiated at the same gamma radiation dosage level thereby establishing the formation of cross-linked polymers and radiolytic degradation products.

EXAMPLE 3

To a 200 ml. of a 1% solution of povidone K-90 was added 0.4 gm. of elemental iodine and the mixture stirred and filtered. The clear filtered solution was irradiated with Cobalt 60 gamma radiation at a dosage level of 30 megarads whereupon it gelled.

A second solution containing 1% povidone K-90, 0.4 gm. of elemental iodine and 0.2 gms. of potassium iodide was irradiated with Cobalt 60 gamma radiation at a dosage level of 30 megarads and gelation was not observed. The second solution had the following properties after irradiation:

| | |
|---|---|
| Appearance | Clear Solution |
| Viscosity | 4.03 |
| Cross-linked Polymers | Absent |
| No. Average Molecular Weight | 91,000 |

These test results establish the desirable protective effect of the iodine-iodide ion component.

EXAMPLE 4

To 1 liter of a 1.0% solution of povidone K-30 was added 0.1 gm. of iodine, 0.02 gms. of potassium iodide and 0.01 gms. of potassium iodate. The mixture was stirred, filtered and irradiated with gamma radiation at a dosage level of 2 megarads. The solution, after irradiation, had a clear appearance and a viscosity of 1.03 at 25° C. Gel permeation chromatography revealed the absence of cross-linked polymers and a numerical average molecular weight of 31,500.

A second povidone solution was prepared to contain the same components as above but the iodide ion content reduced to 0.005 gms. of potassium iodide which represents a two-fold reduction in iodide ion. The protective effect against cross-linkage and radiolysis upon irradiation with gamma radiation was observed and the solution had the following properties:

| Appearance | Clear |
|---|---|
| Viscosity at 25° C. | 1.02 |
| Cross linkage | Absent |
| No. Average Molecular Weight | 31,500 |

EXAMPLE 5

A freshly prepared aqueous solution containing povidone K-30, 2% by weight is mixed with 200 mg. of resublimed reagent-grade iodine which is virtually iodide free and immediately after preparation, an aliquot portion of this solution (Solution A) is irradiated with a gamma radiation dose of 20 megarads. It is found that after irradiation the amber iodine color of solution is discolorized. The presence of radiolysis products and cross-linked polymers is found by gel permeation chromatography together with an increased viscosity over the non-irridiated retained portion which serves as a control solution.

The remainder of the Solution A serves as a reference control (Solution B).

However, when a second aqueous solution (Solution C) of povidone K-30 and iodine is prepared at the same concentrations but adding 0.4% by weight of iodide ions and irradiation, this solution with 20 megarads gamma radiation, the decolorization does not occur. A comparison of the properties of the separate solutions follows:

| Property | SOLUTION A PVP K-30/$I_2$ (iodide-free) Non-Irradiated | SOLUTION B PVP-K-30/$I_2$ (iodide-free) Irradiated | SOLUTION C PVP K-30/$I_2$ (iodide-added) Irradiated |
|---|---|---|---|
| Appearance | Clear-Amber | Clear-Colorless | Clear-Amber |
| Viscosity | 1.02 | 2.31 | 1.01 |
| Cross-linked Polymers | Absent | Present | Absent |
| No. Average Molecular Weight | 31,200 | 45,800 | 31,100 |
| Iodine Content | 9.85% | Absent | 9.72% |

It will be observed that solution C containing the iodine-iodide ion protective composition maintained the iodine content after irradiation at the same dose level and there were no cross-linked polymers formed. Gel permeation chromatography did not reveal the presence of radiolysis and cross-linked polymer by-products which was substantiated by viscosimetric measurements when compared to the non-irradiated solution.

When the above described solutions were prepared to contain 200 mg. of iodate-ion, an amount equal to the iodine concentration, no polymer changes were determined after Cobalt 60 gamma radiation at dosage levels of up to 30 megarads. Gel permeation chromatography and viscosity measurements established the absence of cross-linked polymers and/or radiolysis degradation products.

While the elemental iodine content was completedly destroyed in the iodide-free povidone K-30 iodine Solution A after a radiation dose of 20 megarads, there was only a loss of less than 5% in iodine content when Solution C is irradiated.

The iodine content was also preserved in the preparation containing iodate ion in addition to the iodide ion. Thus the presence of iodate ion improves the shelf-life stability after irradiation of a povidone product when iodine is a desired ingredient.

It was found that the irradiated PVP K-30/$I_2$ preparation containing iodide ions when aged at 40° C. and 80% relative humidity for one month showed a loss of about 20% of the total iodine content. In contrast to this, the preparation containing PVP K-30/iodine, iodide ion and iodate ion revealed virtually no change in iodine content when aged at the same elevated temperature and humidity conditions for the same period. This side-by-side testing adds another dimension of the use of the iodate ion in addition to the iodide ion gamma radiation protective effect.

In practice, it is found that the irradiation of povidone solutions may be carried out by adding to the providone solution a determined amount of iodine and iodide ions each in definite proportion to the other. Thus, for each part by weight of povidone is added from 0.01 to 0.20 parts by weight of iodine, with the preferred amount being 0.10 parts by weight, and from 0.005 to 0.5 parts by weight of iodide ion with a preferred concentration of 0.05 parts by weight.

In general it will be found that for every part of weight of povidone there may be used a total iodine moiety concentration comprising from 0.015 to 1.0 parts by weight of the iodine with iodide or triodide and possibly also with hypiodite, periodate, iodate salts with the preferred concentration of the iodine moiety being 0.15 parts by weight for each part by weight of povidone.

While the invention has been illustrated with respect to particular compositions and particular degrees of irradiation, it is apparent that variations and modifications of the invention can be made. Such variations and modifications are meant to be comprehended within the meaning and scope of the following claims.

What is claimed is:

1. Method for the sterilization of povidone solutions without degradation thereof and without gelation of the povidone, which comprises subjecting a solution of povidone in the presence of iodine and iodide ions to gamma radiation in a dose sufficiently high to cause gelation of said povidone in the absence of said iodine and said iodide ions, said iodine and said iodide ions being present in an amount and in an iodine to iodide ratio sufficient to prevent said gamma radiation dose from causing said povidone to gel, whereby said solution is sterilized without degradation or gelation thereof and without loss of available iodine.

2. Method according to claim 1 wherein the proportion of iodine to iodide ion is between 1:10 and 10:1.

3. Method according to claim 1 wherein the amount of iodine is between about 0.1 and 1% by weight of the amount of said povidone.

4. Method according to claim 1 wherein the proportion of iodine to iodide ion is about 2:1.

5. Method according to claim 1 wherein the source of iodide ions is an inorganic or organic iodide salt.

6. Method according to claim 1 wherein iodate ions are also present.

7. Method according to claim 6 and wherein the source of said iodine is povidone-iodine.

8. Method according to claim 1 wherein the source of said iodine is povidone-iodine.

9. Method according to claim 8 wherein the amount of iodine is between 0.1 and 1% by weight of the amount of said povidone.

10. Method according to claim 1 wherein the proportion of iodine to iodide ion is between 100:1 and 1:100.

11. Method according to claim 10 wherein the amount of iodine is about 0.1% to 20% by weight of the povidone.

12. Method according to claim 1 wherein the source of iodide ions is an inorganic iodide salt.

13. Method according to claim 12 wherein iodate ions are present in an amount by weight substantially equal to the iodide salt.

* * * * *